US00PP25303P2

(12) United States Plant Patent
Zampini

(10) Patent No.: US PP25,303 P2
(45) Date of Patent: Feb. 24, 2015

(54) *PHILADELPHUS* PLANT NAMED 'ROMANIZAM'

(50) Latin Name: *Philadelphus coronarius*
Varietal Denomination: Romanizam

(71) Applicant: LCN Holdings, Inc., Perry, OH (US)

(72) Inventor: James W. Zampini, Madison, OH (US)

(73) Assignee: LCN Holdings, Inc., Perry, OH (US)

( * ) Notice: Subject to any disclaimer, the term of this patent is extended or adjusted under 35 U.S.C. 154(b) by 0 days.

(21) Appl. No.: 13/986,353

(22) Filed: Apr. 23, 2013

Related U.S. Application Data

(60) Provisional application No. 61/687,385, filed on Apr. 24, 2012.

(51) Int. Cl.
*A01H 5/00* (2006.01)

(52) U.S. Cl.
USPC ..... Plt./226

(58) Field of Classification Search
CPC ..... A01H 5/00
USPC ..... Plt./226
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Philadelphus coronaria*, 'Romanizam', that is characterized by its foliage that is spring and summer and turns a golden yellow in fall, its upright, mounded plant habit, and its semi-double white, fragrant flowers.

2 Drawing Sheets

Botanical classification: *Philadelphus coronarius*.
Variety denomination: 'Romanizam'.

BACKGROUND OF THE INVENTION

The present invention relates to a new and distinct cultivar of *Philadelphus coronarius* and will be referred to hereafter by its cultivar name, 'Romanizam'. 'Romanizam' is a new cultivar of mock orange, a shrub grown for use as an ornamental landscape plant.

The new cultivar of *Philadelphus* was discovered as a naturally occurring whole plant mutation by the Inventor in Perry, Ohio in summer of 1997. The new cultivar was discovered growing in a seed bed that had been planted with seed derived from unnamed plants of *Philadelphus coronaria*. The exact parent plants are unknown.

Asexual reproduction of the new cultivar was first accomplished by the Inventor using softwood stem cuttings in summer of 2008 in Perry, Ohio. The characteristics of this cultivar have been determined to be stable and are reproduced true to type in successive generations.

SUMMARY OF THE INVENTION

The following traits have been repeatedly observed and represent the characteristics of the new cultivar as grown outdoors in Perry, Ohio. These attributes in combination distinguish 'Romanizam' as a unique cultivar of *Philadelphus*.

1. 'Romanizam' exhibits large semi-double white, fragrant flowers.
2. 'Romanizam' exhibits a mounded, spreading plant habit with arching branches.

Typical plants of the *Philadelphus coronarius* differ from 'Romanizam' in having smaller single flowers. 'Romanizam' can be compared to the cultivars; 'Icezam' and 'Incnozam' selected by the same Inventor. 'Icezam' differs from 'Romanizam' in having smaller single flowers that are less fragrant, in having a more upright plant habit, and in having variegated foliage. 'Incnozam' differs from 'Romanizam' in having flowers that are smaller and double and more fragrant, in having a more upright plant habit, and in having foliage that exhibits golden yellow fall color. 'Romanizam' can also be compared to the cultivar *Philadelphus×virginalis* 'Minnesota Snowflake' (not patented). 'Minnesota Snowflake' differs from 'Romanizam' in having fully double flowers and a more upright plant habit.

BRIEF DESCRIPTION OF THE DRAWINGS

The accompanying colored photographs illustrate the overall appearance and distinct characteristics of the new *Philadelphus*. The photographs were taken of a two year-old plant as grown outdoors in trial garden in Perry, Ohio.

The photograph in FIG. 1 provides an overall view of the plant habit of two plants of 'Romanizam'.

Figure 1:
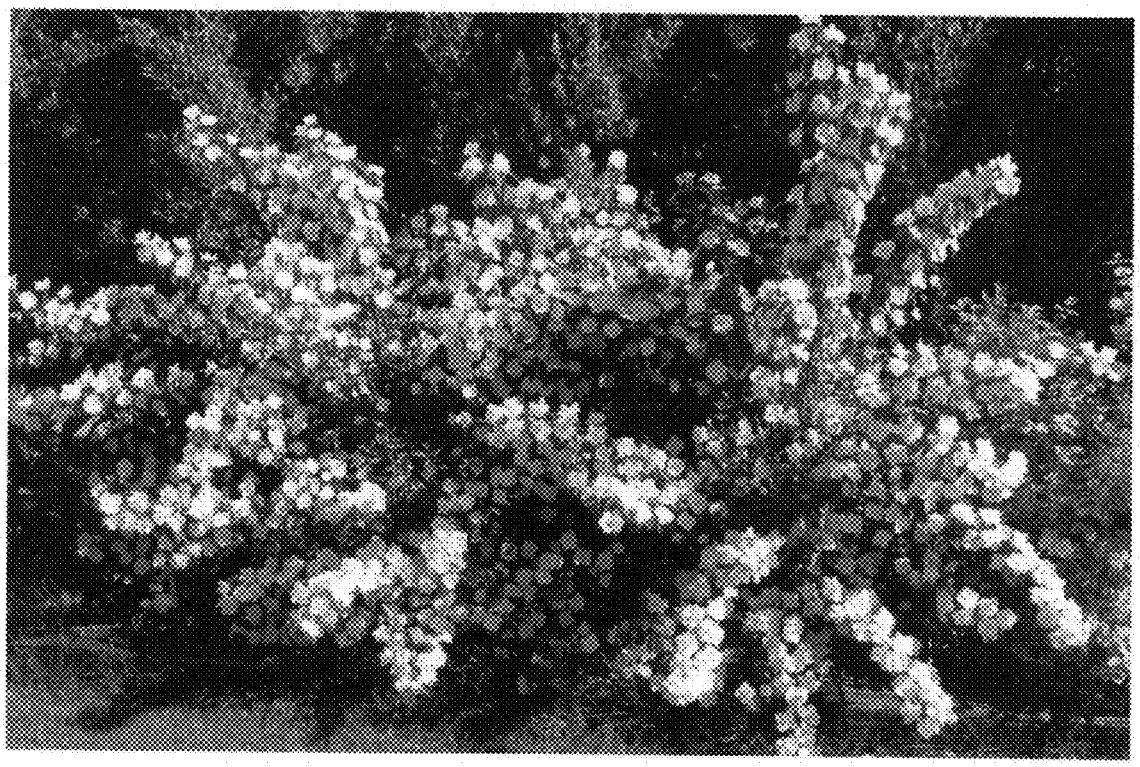
Figure 2:
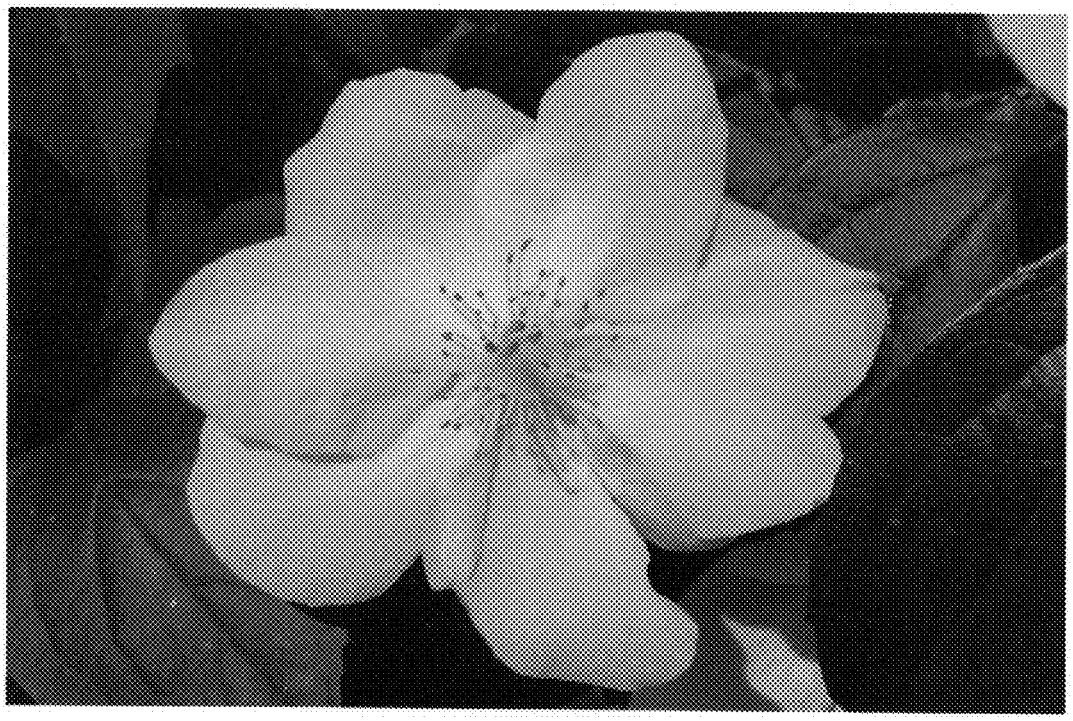

The photograph in FIG. 2 provides a close-up view of a flower of 'Romanizam'.

Figure 3:
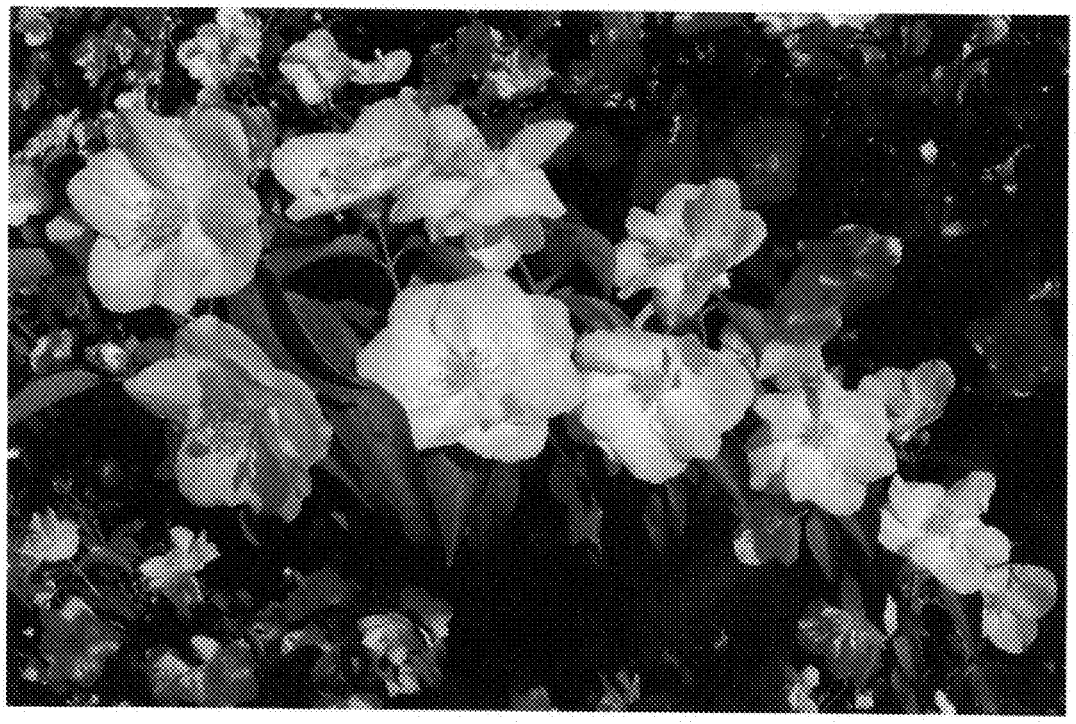

The photograph in FIG. 3 provides a close-up view of an inflorescence of 'Romanizam'.

The colors in the photograph may differ slightly from the color values cited in the detailed botanical description, which accurately describe the colors of the new *Philadelphus*.

DETAILED BOTANICAL DESCRIPTION

The following is a detailed description of 2 year-old plants of the new cultivar as grown outdoors in full sun in a trial plot in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for at least 4 weeks in late May to early June in Ohio.

*Plant type*.—Deciduous shrub.

*Plant habit*.—Mounded, spreading with arching branches.

*Plant size*.—Reaches about 2.4 to 2.5 m (8 to 10 feet) in height and width at four years of age in the landscape.

*Cold hardiness*.—At least to U.S.D.A. Zone 4.

*Diseases and pests*.—No susceptibility or resistance to diseases or pests has been observed.

*Root description*.—Fibrous, moderately dense.

*Propagation*.—Softwood stem cuttings.

*Growth rate*.—Vigorous.

Stem description:

*Shape*.—Oval.

*Stem color*.—New growth; 144A, mature wood; a blend of 165A and 161C.

*Stem size*.—Basal branches; an average of 2.4 m in length and 2 mm in diameter, lateral branches; an average of 22 cm in length and 2 mm in diameter.

*Stem surface*.—New growth; glabrous, mature wood; slightly exfoliating (shreddy).

*Stem aspect*.—Upright to arching.

*Branching*.—Average of 6 main stems and an average of 8 lateral branches per main stem, branch internode length; an average of 3 cm.

Foliage description:

*Leaf shape*.—Ovate.

*Leaf division*.—Simple.

*Leaf base*.—Rounded.

*Leaf apex*.—Acuminate.

*Leaf fragrance*.—None.

*Leaf venation*.—Primarily pinnate, color matches leaf coloration on upper and lower surface.

*Leaf margins*.—Serrate.

*Leaf arrangement*.—Opposite.

*Leaf attachment*.—Petiolate.

*Leaf surface*.—Matte on upper and lower surface, upper surface sparsely covered with very short hairs up to 1 mm in length and NN155D in color, lower surface densely covered with pubescence up to 1.5 mm in length and 155C in color.

*Leaf internode length*.—Up to 5 cm.

*Leaf size*.—An average of 6 cm in length and 3 cm in width.

*Leaf quantity*.—An average of 12 per stem.

*Leaf color*.—Newly expanded leaves upper and lower surface; 144A, mature leaves upper and lower surface; 146A.

*Petioles*.—Up to 7 mm in length and 1 mm in width, color 144A, matte surface, moderately covered with soft hairs up to 1.5 mm in length and NN155D in color.

*Stipules*.—Up to 1 cm in length and 3 mm in width, a blend of 144C and 143C in color, both surfaces glabrous.

Inflorescence description:

*Inflorescence type*.—Racemes of about 14 semi-double flowers, single or occasionally in pairs.

*Inflorescence size*.—Raceme is an average of 35 cm in diameter and 12 cm in diameter.

*Flower buds*.—Globose in shape, an average of 1.7 cm in depth and diameter, 155B in color with sepal portion a color between 138A and 144A.

*Flower fragrance*.—Fragrant, orange scented.

*Lastingness of flowers*.—About 10 days.

*Flower aspect*.—Outward to upright.

*Flower quantity*.—An average of 14 per lateral stem, an average of 80 per main stem (including laterals).

*Flower type*.—Rotate.

*Flower size*.—Average of 5.7 cm in diameter and 2 cm in depth.

*Peduncles*.—Average of 3 cm in length and 2 mm in diameter, color 144A, glabrous surface, oval in shape.

*Pedicels*.—None, sessile to peduncle.

*Calyx*.—Rotate in shape with lower portion fused, an average of 8 mm in depth and 2 cm in width.

*Sepals*.—4, ovate in shape, acuminate apex with mucronate tip, cuneate and fused base, entire margin, an average of 1 cm in length and 8 cm in width, color on upper and lower surface when opening and mature a color between 144A and 138A, slightly pubescent on both surfaces.

*Petals*.—4, un-fused, ovate in shape, margin undulating with occasional shallow serrations, apex acute to rounded, an average of 2.8 cm in length and width, outer and inner surface is glabrous, color of inner and outer surface when opening and mature; NN155C.

*Petaloids*.—An average of 4 (plus occasionally 1 to 2 smaller ones), un-fused, variable in shape; primarily elliptic or ovate, margin entire, apex broadly acute, an average of 2.5 cm in length and 1.8 cm in width, outer and inner surface is glabrous, color of inner and outer surface when opening and mature; NN155C.

Reproductive organs:

*Gynoecium*.—4 pistils, united, about 1.2 cm in length, style is an average of 1 cm in length, and NN155A in color, stigma is 155A in color, ovary is inferior and surrounded by nectar secreting disk; 145C in color, 5 mm in diameter and 7 mm in length.

*Androcoecium*.—About 35 stamens, filaments are 155B in color and an average of 1.5 cm in length, anthers are 160B in color, an average of 3 mm in length, basifixed and oblong in shape, pollen is moderate in quantity and 161C in color.

*Fruit and seed*.—Fruit; 4-valved capsule, about 7 mm in length and width, dries to 199C in color, seed: none observed.

It is claimed:

1. A new and distinct cultivar of *Philadelphus* plant named 'Romanizam' as herein illustrated and described.

* * * * *